United States Patent
Mizuno et al.

(10) Patent No.: US 6,632,943 B2
(45) Date of Patent: Oct. 14, 2003

(54) PROCESS FOR PRODUCTION OF OPTICALLY ACTIVE PYRROLOAZEPINE DERIVATIVES

(75) Inventors: Akira Mizuno, Kyoto (JP); Kazuto Sekiuchi, Tatebayashi (JP); Takushi Nagata, Yokohama (JP); Teruo Muraishi, Yokohama (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 20 days.

(21) Appl. No.: 09/913,262

(22) PCT Filed: Dec. 14, 2000

(86) PCT No.: PCT/JP00/08850

§ 371 (c)(1),
(2), (4) Date: Aug. 10, 2001

(87) PCT Pub. No.: WO01/44251

PCT Pub. Date: Jun. 21, 2001

(65) Prior Publication Data

US 2002/0143006 A1 Oct. 3, 2002

(30) Foreign Application Priority Data

Dec. 16, 1999 (JP) ............................................ 11/356955

(51) Int. Cl.$^7$ ............................................ C07D 487/04
(52) U.S. Cl. ............................................ 540/521
(58) Field of Search ............................................ 540/521

(56) References Cited

U.S. PATENT DOCUMENTS

| | | | |
|---|---|---|---|
| 5,756,790 A | 5/1998 | Mukaiyama et al. | 556/32 |
| 5,962,448 A | 10/1999 | Mizuno et al. | 514/215 |

*Primary Examiner*—Brenda Coleman
(74) *Attorney, Agent, or Firm*—Crowell & Moring LLP

(57) ABSTRACT

It is provided a method for preparing the pyrroloazepine derivatives, especially in optically active form useful as drugs, by low-priced and simple method and in industrial applicable scale, represented by the following formula (I):

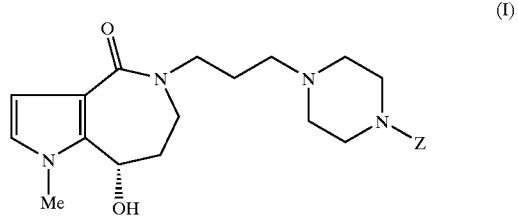

wherein Z represents optionally substituted phenyl group, which comprises;
a process for the asymmetric reduction of ketone compound with metal hydride compound and alcohol compound in the presence of optically active cobalt complex catalyst, and
a process for the purification of the resulting compound.

48 Claims, No Drawings

PROCESS FOR PRODUCTION OF OPTICALLY ACTIVE PYRROLOAZEPINE DERIVATIVES

This application is a national stage entry under 35 U.S.C §371 of PCT/JP00/08850, filed Dec. 14, 2000.

TECHNICAL FIELD

The present invention relates to a method for preparing optically active pyrroloazepine derivatives useful as drugs or raw materials as well as intermediates for the synthesis of these drugs. More particularly, it relates to a method for preparing optically active pyrroloazepine derivatives by asymmetric reduction methods.

BACKGROUND ART

Pyrrolo[3,2-c]azepine derivatives are important compounds useful as drugs for treatment of cardiovascular disease or raw materials as well as intermediates for the synthesis of these drugs. For example, International Patent Publication Number WO97/20845 disclosed pyrroloazepine derivatives having strong serotonin-2 receptor antagonistic action of excellent selectivity. The compounds are useful, for example, for the prevention or treatment of ischemic heart diseases such as angina pectoris, arrhythmia, myocardial infarction, cardiac insufficiency and post-PTCA (Percutaneous Transluminal Coronary Angioplasty) restenosis; cerebrovascular disturbances such as cerebral infarction and cerebral sequelae after subarachnoid hemorrhage; peripheral circulatory disturbances such as arteriosclerosis obliterans, Raynaud's disease and Buerger's disease; and hypertension.

Further, Japanese Laid-open Patent Publication Number Hei 10-251258disclosed compounds having pyrrolo[3,2-c] azepine skeleton for treatment of cardiovascular diseases.

Among these pyrrolo[3,2-c]azepine derivatives useful for drugs, there are some compounds having asymmetric carbon atoms in their molecule. For example, several pyrrolo[3,2-c]azepine derivatives disclosed in International Patent Publication Number WO97/20845 have a hydroxyl substituent at the 8-position carbon atom and therefore, these compounds have one pair of enantiomers due to the presence of asymmetric carbon atom at the 8-position.

It is well known that in the case of the compound having one pair of enantiomers, pharmacological activities and toxicities of both enantiomers sometimes greatly differs from each other (C. C. Pfeiffer, *Science,* Vol. 124, 29 (1956); F. P. A. Lehmann, *Quant. Struct. Act. Relat.,* Vol. 6, 57 (1987)). Therefore, when pharmacological activities and toxicities of optically active compounds are different from each other, it is demanded to select one optically active compound having more effectiveness and safety margin in comparison to their pharmacological activities, pharmacokinetics, side effects and toxicities, totally.

For the methods to obtain the optically active compound, it is divided broadly into two methods. That is, by mean of optical resolution method and asymmetric synthesis method for the desired optically active compound. As the former method, it is generally known a method for separating racemic compounds by using optically active column chromatography, by recrystallization of diastereoisomers which is derived by introducing the group having other asymmetric center or by reacting with other optically active acids or bases, by using enzyme reaction, and so on. However, these methods have a disadvantage that the chemical yield of the desired optically active compound is 50% at maximum.

As the later method, asymmetric synthesis is a typical method to obtain the desired optically active compound selectively. Examples of this asymmetric synthesis method are a method for synthesis of the desired optically active compound by using optically active sugars or amino acids as the starting materials and utilizing their stereo arrangement, a method for deriving to optically active compound from its precursor which is non optically active compound by introducing the group stereoselectively or by reducing stereoselectively, and so on. The chemical yield of the desired optically active compound by asymmetric synthesis is 100% theoretically and that makes this method advantageous; however, the optical yield is greatly changed by the substrate to be used and the optical and chemical yields are also greatly changed by the reaction conditions such as reagents, solvents, concentrations of substrate, and reaction temperature to be used. Therefore, there are extremely difficult to determine the reaction systems or the reaction conditions to be used for the asymmetric synthesis.

Furthermore, it is necessary to conduct the reaction at super-low temperature to obtain high optical yield of the asymmetric synthesis. The operation such as preparing a reagent is very complicated and the starting materials or reagents necessary for the production are expensive. These points are recognized to be disadvantages at the presence. That is, it is important to select the best reaction conditions for every substrate to be used in the asymmetric synthesis. Further, in the case of the asymmetric synthesis using the asymmetric catalyst, it is important to select the best asymmetric catalyst and reaction conditions suitable for the individual substrate.

For example, in the above-mentioned International Patent Publication Number WO97/20845, several synthetic methods for preparing the optically active pyrrolo[3,2-c]azepine compounds having a hydroxyl substituent at the 8-position are disclosed. Nevertheless, these methods are not sufficient for the industrial methods in operational and economical standpoints, and further improvements are required. In the Patent Publication, the methods for preparing the optically active pyrroloazepine derivatives from racemic pyrroloazepine derivatives by using optically active column chromatography, by recrystallization of salts with optically active acids, or by enzyme reaction are disclosed, and the desired optically active pyrroloazepine derivatives can be prepared by using one of these methods or the combination thereof. Although, these methods are simple methods for preparing the optically active pyrroloazepine derivatives, the chemical yield is low and it is not economically sufficient.

Further, other methods for preparing the optically active pyrroloazepine derivatives, for example, an asymmetric reduction method of ketone compounds, i.e., precursors of pyrroloazepine derivatives, using boran as reducing reagent with optically active oxazaborollidine catalyst, or using ruthenium complex catalyst for hydrogen transfer reduction, is disclosed.

However, these methods have several disadvantages, such as complication in reagents' preparing, requirement on selecting the strict reaction conditions, high cost of reagents and low chemical yield, and are not economically sufficient.

Under these circumstances, the purpose of the present invention is to provide the methods for preparing the optically active pyrroloazepine derivatives useful for drugs in simple, economical as well as industrial applicable scale. More specifically, the present invention is to provide the simple and economical methods for preparing the optically active pyrrolo[3,2-c]azepine compounds having a hydroxyl substituent at the 8-position from their precursors, i.e., ketone compounds having carbonyl group at the 8-position, by the asymmetric reduction.

The present inventors have proceeded with extensive investigation to develop the industrial applicable methods for preparing the optically active pyrroloazepine derivatives, and it is found that the desired optically active pyrroloazepine compounds can be synthesized easily in good chemical and optical yields by combining the asymmetric reduction process of ketone compounds using metal hydride compound and alcohol compound in the presence of optically active cobalt complex catalyst, and a purification process of the resulting pyrroloazepine compound. The present invention has been completed based on the findings mentioned above.

DISCLOSURE OF INVENTION

Accordingly, as one aspect of the present invention, it is provided a method for preparing the optically active pyrroloazepine derivatives represented by the following formula (I):

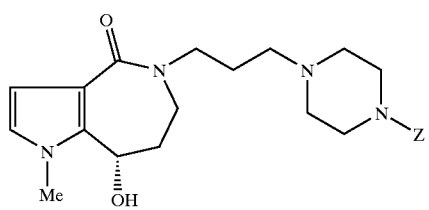

(I)

wherein Z represents optionally substituted phenyl group, which comprises;
a process for the asymmetric reduction of the ketone compound represented by the following formula (II):

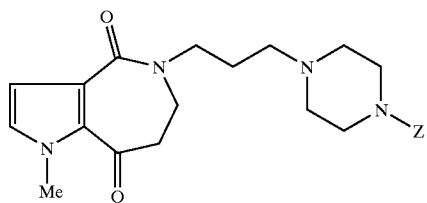

(II)

wherein Z has the same meaning mentioned above, by using metal hydride compound and alcohol compound in the presence of optically active cobalt complex catalyst, and,
a process for the purification of the resulting compound.

As another aspect of the present invention, it is provided a method for preparing the optically active pyrroloazepine derivatives represented by the following formula (I):

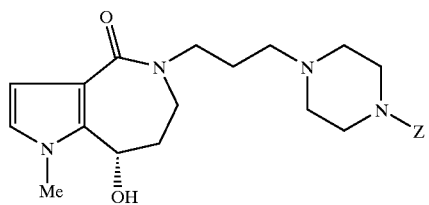

(I)

wherein Z has the same meaning mentioned above, which comprises;

a process for the asymmetric reduction of the ketone compound represented by the following formula (III):

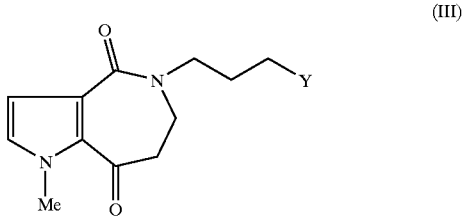

(III)

wherein Y represents a halogen atom, by using metal hydride compound and alcohol compound in the presence of optically active cobalt complex catalyst to obtain the optically active alcohol compound represented by the following formula (IV):

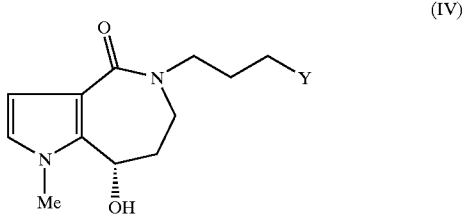

(IV)

wherein Y has the same meaning mentioned above,
a process for reacting the resulting alcohol compound of the formula (IV) with the piperazine compound represented by the following formula (V) or salt thereof:

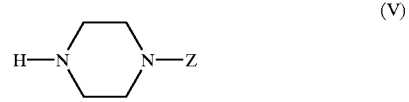

(V)

wherein Z has the same meaning mentioned above, and,
a process for the purification of the resulting compound.

As still another aspect of the present invention, it is provided a method for preparing the optically active pyrroloazepine derivatives of the formula (I), wherein the ligand of optically active cobalt complex catalyst is one enantiomer of the following formula (VI):

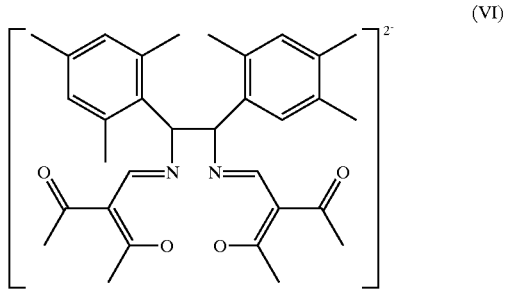

(VI)

wherein this formula represents an optical active compound,
in which two mesityl groups are located in trans form to each other,
in which said enantiomer is derived from the protonated compound having levorotatory (the optical rotatory power is negative) represented by the following formula (VII).

(VII)

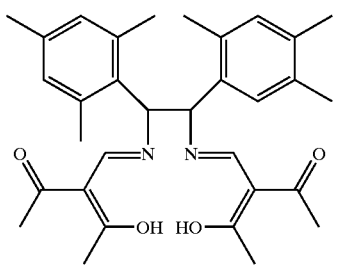

As still further aspect of the present invention., it is provided a method for preparing the optically active pyrroloazepine derivatives of the formula (I), wherein cobalt atom of optically active cobalt complex catalyst is divalent cobalt [Co(II)] or trivalent cobalt [Co(III)].

As still further aspect of the present invention, it is provided a method for preparing the optically active pyrroloazepine derivatives of the formula (I), wherein alcohol compound used in the reaction is tetrahydrofurfuryl alcohol.

As still another aspect of the present invention, it is provided a method for preparing the optically active pyrroloazepine derivatives of the formula (I), wherein the asymmetric reduction is conducted in solvent containing tetrahydrofuran.

BEST MODE FOR CARRYING OUT THE INVENTION

The optically active pyrroloazepine derivatives represented by the formula (I) of the present invention can be prepared in accordance with the following reaction scheme.

In the reaction scheme, the groups Y and Z have the same meanings mentioned above.

of the formula (I) comprising (a) a process of the asymmetric reduction of the ketone compound of the formula (II) with metal hydride compound and alcohol compound in the presence of optically active cobalt complex catalyst, and (b) a process for the purification of the resulting compound obtained in process (a).

The ketone compound of the formula (II) to be used in the method 1 can be obtained by the reaction of the ketone compound of the formula (III) with the piperazine compound of the formula (V) or salt thereof.
Method 2

In accordance with this method 2, it is provided a method for preparing the optically active pyrroloazepine derivatives of the formula (I) comprising (a) a process of the asymmetric reduction of the ketone compound of the formula (III) with metal hydride compound and alcohol compound in the presence of optically active cobalt complex catalyst to obtain the alcohol compound of the formula (IV), (b) a process for reacting the resulting alcohol compound of the formula (IV) with the piperazine compound represented by the formula (V) or salt thereof, and (c) a process for the purification of the resulting compound obtained in process (b).

The present invention also provides a method for preparing the optically active compounds of the formula (IV), which comprises conducting the asymmetric reduction of the ketone compound of the formula (III) with metal hydride compound and alcohol compound in the presence of optically active cobalt complex catalyst:.

Optically active cobalt complex catalyst, metal hydride compound and alcohol compound used in the asymmetric reduction of the present invention, are used of these described in Japanese Laid-open Patent Publication Number Hei 9-151143.

The present invention is described in more detail by illustrating the each method.

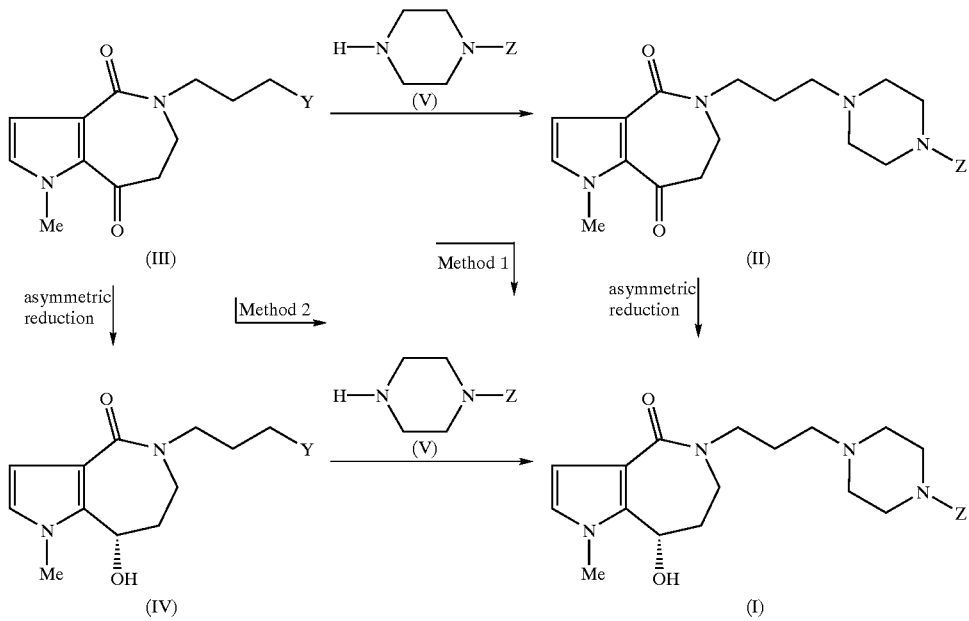

That is, the present invention is to provide following two methods for preparing the optically active pyrroloazepine derivatives of the formula (I).
Method 1

In accordance with this method 1, it is provided a method for preparing the optically active pyrroloazepine derivatives The method 1 of the present invention is conducted by (a) a process of the asymmetric reduction of the ketone compound of the formula (II) with metal hydride compound and alcohol compound in the presence of optically active cobalt complex catalyst, and (b) a process for the purification of the resulting compound obtained in process (a) to obtain the compound of the formula (I), represented by the following reaction scheme.

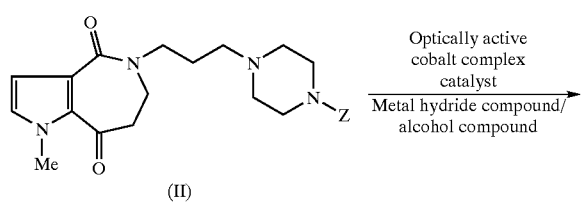

(II)

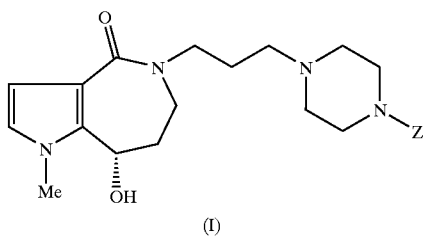

(I)

wherein Z represents optionally substituted phenyl group.

The examples of the optionally substituted phenyl group include unsubstituted phenyl group; phenyl group substituted by halogen atom such as fluorine, chlorine and so on; phenyl group substituted by alkoxy group such as methoxy group; phenyl group substituted by hydroxyl group and its acyl derivatives; phenyl group substituted by straight or branched alkyl group; phenyl group substituted by nitro group, and the like.

The method 2 of the present invention is conducted by (a) a process of the asymmetric reduction of the ketone compound of the formula (III) with metal hydride compound and alcohol compound in the presence of optically active cobalt complex catalyst to obtain the alcohol compound of the formula (IV) as intermediate, (b) a process for reacting the resulting alcohol compound of the formula (IV) with the piperazine compound represented by the formula (V) or salt thereof, and then (c) a process for the purification of the resulting compound obtained in process (b) to obtain the compound of the formula (I).

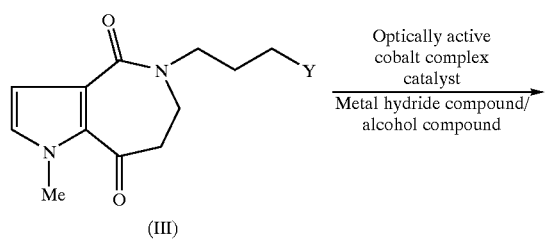

(III)

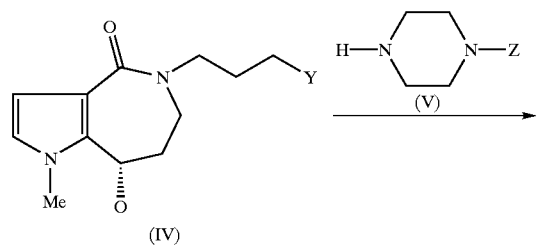

(IV)

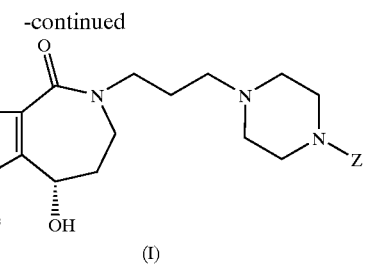

(I)

wherein Y represents a halogen atom and Z has the same meaning mentioned above.

The suitable halogen atom represented by "Y" in the ketone compound of the formula (III) may include chlorine, bromine and iodine atom, and a chlorine atom is most preferable.

Although preparation of the optically active pyrroloazepine derivatives of the formula (I) of the present invention may be conducted by the above-mentioned two methods, and both methods are suitable for the production of the optically active pyrroloazepine derivatives of the formula (I), the method 2 is more preferable in view of simple operation system.

The examples of optically active cobalt complex catalyst to be used in the present invention may include optically active cobalt complex catalyst described in Japanese Laid-open Patent Publication Number Hei 9-151143. The ligands of the optically active cobalt complex catalyst may be optically active ligands described in said Patent Publication. Among them, one enantiomer divided from the following one pair of enantiomers ((S, S)-form, or (R, R)-form) represented by the following formula (VI):

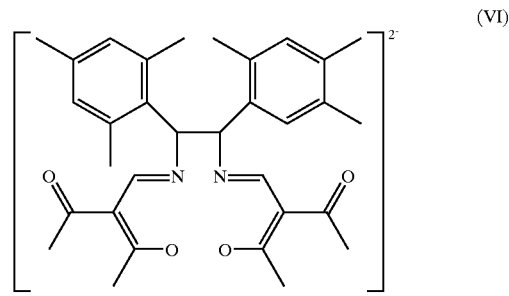

(VI)

wherein this formula represents an optically active compound, in which two mesityl groups are located in trans form to each other, may be preferably used as a ligand.

This ligand, i. e., one enantiomer of the formula (VI) can be obtained from the protonated compound represented by the following formula (VII):

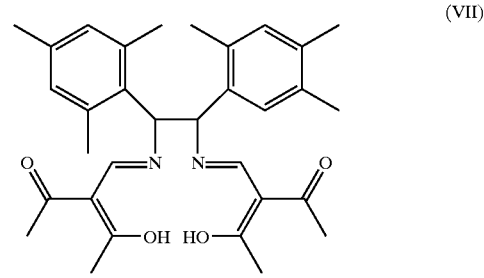

(VII)

wherein this formula represents an optically active compound, in which two mesityl groups are located in trans form to each other, having levorotatory [for example, optical purity of the compound (VII) is 99% e.e.; and specific rotatory power is −186°; $[\alpha]_D^{28}$ −186° (c=1.0 in chloroform)].

Cobalt atom of optically active cobalt complex catalyst is divalent cobalt [Co(II)] or trivalent cobalt [Co(III)]. The optically active cobalt (II) complex catalyst, in which the cobalt atom is divalent cobalt [Co(II)], is represented by the following formula (VIII).

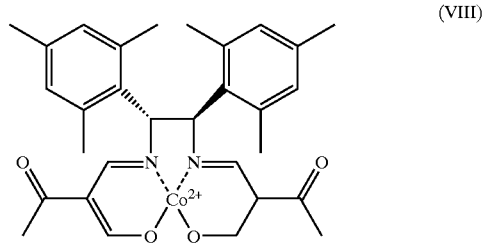

(VIII)

wherein, the compound represented by this formula or one protonated enantiomer having levorotatory (the optical rotatory power is negative) is used as the optically active ligand.

The optically active cobalt (III) complex catalyst, in which the cobalt atom is trivalent cobalt [Co(III)], is represented by the following formula (IX).

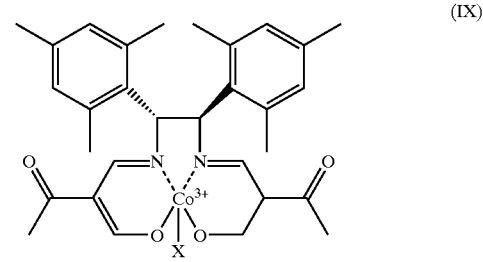

(IX)

wherein, X represents a halogen atom or an acetoxy group, the compound represented by this formula or one protonated enantiomer having levorotatory (the optical rotatory power is negative) is used as the optically active ligand.

The amount of optically active cobalt complex catalyst used in the present invention may vary in accordance with ketone compound as substrate, metal hydride compound, alcohol compound and solvent to be used. It is desirable to use optically active cobalt complex in a proportion of 0.05 to 10.0 mol %, and more preferably 0.1 to 2.0 mol % per 1 mole of the ketone compound.

The examples of metal hydride compound used in the present invention include those described in Japanese Laid-open Patent Publication Number Hei 9-151143. Among them, sodium borohydride is preferably used in view of operation system. The amount of sodium borohydride is in a proportion of 1.0 to 2.5 moles per 1 mole of the ketone compound.

The examples of alcohol compound used in the present invention may include those described in Japanese Laid-open Patent Publication Number Hei 9-151143. Among them, tetrahydrofurfuryl alcohol is preferably used. The amount of the tetrahydrofurfuryl alcohol is in a proportion of 4 to 6 moles per 1 mole of the ketone compound.

In the practice of the present invention, the reaction is preferably carried out in a liquid phase. A solvent may be used if necessary. Useful examples of the solvent are those described in Japanese Laid-open Patent Publication Number Hei 9-151143, and for example, may include halide solvent such as chloroform; aromatic solvent such as toluene; ether solvent such as tetrahydrofuran; and so on. Preferred solvent is tetrahydrofuran. The highly dehydrated solvents or commercially available solvents may also be used in this reaction. The amount of the solvent is generally 1 to 100 L per 1 mole of the ketone compound. The optically active pyrroloazepine derivatives can be obtained in high chemical and optical yields when solvent is used in the range mentioned above.

The reaction temperature of this asymmetric reduction process is generally −100° C. to 50° C., preferably −80° C. to 30° C., more preferably −60° C. to 10° C. There is an advantage that the reaction may also be carried out under simple condition such as ice cooling and still high asymmetric yield is obtained. The reaction can be carried out under normal atmospheric pressure and preferably under nitrogen or argon gas atmosphere for stability of catalyst and compound to be produced. The reaction time of the asymmetric reduction is generally 10 minutes to 5 days. Progress of the reaction can be monitored by taking samples from the reaction mixture at intervals and analyzing them by thin layer chromatography (TLC), high-performance liquid chromatography (HPLC) or the like, and the reaction may be terminated when signal of the starting material, i.e., ketone compound is disappeared.

In the method 2 of the present invention, the reaction of the alcohol compound of the formula (IV), which is obtained by the asymmetric reduction of the ketone compound (III), with the piperazine compound represented by the formula (V) or salt thereof to obtain the optically active pyrroloazepine derivatives, can be carried out in the solvent such as methanol, ethanol, dimethylformamide, dimethyl sulfoxide, acetonitrile, propionitrile, acetone, 2-butanone, tetrahydrofuran, dioxane, toluene and the like. The reaction may be carried out, if necessary, in the presence of organic base such as triethylamine, pyridine, collidine, potassium t-butoxide and the like, or inorganic base such as potassium carbonate, sodium carbonate, sodium hydrogen carbonate, sodium hydroxide, sodium hydride and the like. Further, the reaction may also be carried out, if necessary, in the presence of an alkali iodide such as potassium iodide, sodium iodide and the like.

Collection and purification of the desired optically active pyrroloazepine derivatives from the reaction mixture may be performed by the well-known conventional manner such as adsorption, extraction, recrystallization, column chromatography and the like.

EXAMPLES

The present invention is illustrated in more detail by way of the following examples, but it is to be noted that the present invention is not limited by these Examples in any way.

In the following Examples, silica gel column chromatography was performed by silica gel No. 9385 by Merck Co., Ltd.

Optical purity was analyzed by high-performance liquid chromatography (optically active column: CHIRALPAK AD Φ4.6 mm×250 mm by Daicel Chemical Industries, Ltd.) under following conditions.

Column temperature: 40° C.
Mobile phase: Hexane/ethanol/methanol/diethylamine=70/10/20/0.1
Flow rate: 1.0 mL/minute
Detective wavelength: 254 nm NMR spectrum was measured by ALPHA-500 (500 MHz) (JEDL Ltd.) in $CDCl_3$ using TMS as internal standard, and the value was indicated in $\delta_{ppm}$.

The optical rotation was measured by DIP-360 (Nihon Bunkoh Kogyo, Ltd.) in methanol solution.

Example 1

Synthesis by the Method 1

Synthesis of (S)-5-[3-[4-(4-fluorophenyl)piperazin-1-yl]propyl]-8-hydroxy-1-methyl-1,4,5,6,7,8-hexahydropyrrolo[3,2-c]azepin-4-one from 5-[3-[4-(4-fluorophenyl)piperazin-1-yl]propyl]-1-methyl-1,4,5,6,7,8-hexahydropyrrolo[3,2-c]azepine-4,8-dione by the asymmetric reduction using optically active cobalt (II) complex (a) Preparation of Reducing Reagent 170 mg (4.5 mmol) of sodium borohydride was charged in a first reactor, then replaced the atmosphere with a nitrogen gas, and 6 mL of chloroform was added. To this mixture was added 0.87 mL (9.0 mmol) of tetrahydrofurfuryl alcohol dropwise under stirring and ice-cooling, and the mixture was stirred for 2 hours under the same temperature.

(b) Asymmetric Reduction 1.4 mg (0.0025 mmol; 1 mol %) of optically active cobalt (II) complex of the formula (VIII) and 99.6 mg (0.25 mmol) of 5-[3-[4-(4-fluorophenyl)piperazin-1-yl]propyl]-1-methyl-1,4,5,6,7,8-hexahydropyrrolo[3,2-c]azepine-4,8-dione were added in a second reactor. Then, the atmosphere was replaced with a nitrogen gas, and the mixture was dissolved in 15 mL of tetrahydrofuran (THF). To this mixture was added 0.6 mL of the reducing reagent prepared in process (a) dropwise, and the mixture was stirred for 20 minutes under ice-cooling. Then, 0.6 mL of the reducing reagent prepared in process (a) was added to the reaction mixture and the mixture was stirred for 40 minutes under ice-cooling. Aqueous sodium hydrogen carbonate solution was added to the reaction mixture and extracted with dichloromethane. The extract was washed with saline solution and dried over sodium sulfate. The solvent was removed under reduced pressure and the residue was purified by silica gel column chromatography (eluent; dichloromethane:methanol=9:1) to give 92 mg (yield: 92%; optical purity: 85% e.e.) of the title compound.

Appearance: pale yellow crystalline powder

Melting point: 167.5–168.5° C.

NMR: 1.84(2H, q, J=7.3 Hz), 1.85(1H, br), 2.22(2H, m), 2.46(1H, d, J=7.3 Hz), 2.61(4H, m), 3.12(4H, m), 3.35(1H, dd, J=7.3 Hz & 15.3 Hz), 3.56–3.71(3H, m), 3.73(3H, s), 4.92(1H, m), 6.62(1H, d, J=3.1 Hz), 6.71(1H, d, J=3.1 Hz), 6.87(1H, m), 6.95(1H, m).

Example 2

Synthesis by the Method 2

Synthesis of (S)-5-[3-[4-(4-fluorophenyl)piperazin-1-yl]propyl]-8-hydroxy-1-methyl-1,4,5,6,7,8-hexahydropyrrolo[3,2-c]azepin-4-one from 5-(3-chloropropyl)-1-methyl-1,4,5,6,7,8-hexahydropyrrolo[3,2-c]azepine-4,8-dione by the asymmetric reduction using optically active cobalt (II) complex and followed by the reaction of the resulting alcohol compound with piperazine compound (a) Preparation of Reducing Reagent 688 mg (18.2 mmol) of sodium borohydride was charged in a first reactor, then replaced the atmosphere with a nitrogen gas, and 21.8 mL of chloroform was added. To this mixture was added 5.13 mL (53.0 mmol) of tetrahydrofurfuryl alcohol dropwise under stirring and ice-cooling, and the mixture was stirred for 3 hours under the same temperature.

(b) Asymmetric Reduction 17.2 mg (0.03 mmol; 0.3 mol %) of optically active cobalt (II) complex of the formula (VIII) and 2.54 g (10.0 mmol) of 5-(3-chloropropyl)-1-methyl-1,4,5,6,7,8-hexahydropyrrolo[3,2-c]-azepine-4,8-dione were added in a second reactor, then the atmosphere was replaced with a nitrogen gas, and the mixture was dissolved in 100 mL of THF. To this mixture was added the reducing reagent prepared in process (a) dropwise at −8° C. of reaction bath temperature and the reaction mixture was stirred for 3 hours at −8° C. The reaction mixture was washed with a mixed solution of 40 mL of saturated saline solution and 8 mL of water, and further washed with 40 mL of saturated saline solution, and dried over magnesium sulfate. The solvent was removed under reduced pressure to give 6.16 g (optical purity: 83.5% e.e.) of (S)-5-(3-chloropropyl)-8-hydroxy-1-methyl-1,4,5,6,7,8-hexahydropyrrolo[3,2-c]azepin-4-one as pale brown crystalline.

(c) Reaction with Piperazine Compound

A suspension of 6.16 g of crystalline obtained in (b) above, 1.98 g (11 mmol) of 1-(4-fluorophenyl)piperazine, 2.76 g (20 mmol) of potassium carbonate and 3.0 g (20 mmol) of potassium iodide in 20 mL of acetonitrile was refluxed for 9 hours. After the reaction mixture was cooled down to room temperature, 20 mL of water was added. Separated organic layer was concentrated under reduced pressure, and the water layer was extracted with 20 mL of chloroform. The resulting residue from the organic layer was dissolved with the chloroform extract and the chloroform layer was washed with 10 mL of half saturated saline solution twice and with 10 mL of water, and then dried over sodium sulfate. The solvent was removed under reduced pressure, and the residue was recrystallized from 2-propanol twice to give 2.59 g [yield: 64.6% (2 steps); optical purity: 99.1% e.e.] of the title compound.

Specific rotatory power $[\alpha]_D^{20}$:−7.4° (c=3.0, methanol)

Example 3

Synthesis by the Method 1

Synthesis of (S)-5-(3-chloropropyl)-8-hydroxy-1-methyl-1,4,5,6,7,8-hexahydropyrrolo[3,2-c]azepin-4-one by the asymmetric reduction using the optically active cobalt (III) complex (a) Preparation of Reducing Reagent 170 mg (4.5 mmol) of sodium borohydride was charged in a first reactor, then the atmosphere was replaced with a nitrogen gas, and 6 mL of chloroform was added. To this mixture was added 1.31 mL (13.5 mmol) of tetrahydrofurfuryl alcohol dropwise under stirring and ice-cooling, and the mixture was stirred for 3 hours under the same temperature.

(b) Asymmetric Reduction 127 mg (0.5 mmol) of 5-(3-chloropropyl)-1-methyl-1,4,5,6,7,8-hexahydropyrrolo[3,2-c]azepine-4,8-dione was added in a second reactor, then the atmosphere was replaced with a nitrogen gas, and the mixture was dissolved in 2.5 mL of THF. To this mixture was added a solution of 1.6 mg (0.0025 mmol; 0.5 mol %) of optically active cobalt (III) complex of the formula (IX) [in the formula, X is a bromine atom] in 2.5 mL of THF, and the reaction mixture was stirred for 30 minutes under ice-cooling. Then, to this mixture was added 1.3 mL of the reduction reagent prepared in process (a) dropwise and stirred for 45 minutes under ice-cooling. Phosphate buffer solution (pH 6.0) was added to the reaction mixture and extracted with dichloromethane. The extract was washed with saline solution and dried over sodium sulfate. The solvent was removed under reduced pressure and the residue was purified by silica gel column chromatography (eluent; hexane:ethyl acetate=1:9) to give 123 mg (yield: 96%; optical purity: 83.5% e.e.) of the title compound.

NMR: 2.08(2H, q, J=6.7 Hz), 2.18–2.29(2H, m), 2.59(1H, d, J=7.3 Hz), 3.34(1H, dd, J=7.9 Hz & 15.2 Hz), 3.59(2H, t, J=6.7 Hz), 3.63–3.72(3H, m), 3.72(3H, s), 4.92(1H, m), 6.59(1H, d, J=2.4 Hz), 6.64(1H, d, J=2.4 Hz).

Example 4

Using 1.8 mg (0.0025 mmol; 0.5 mol %) of optically active cobalt (III) complex of the formula (IX) [in the formula, X is an iodine atom] instead of optically active cobalt (III) complex of the formula (IX) [in the formula, X is a bromine atom] in the Example 3, 126 mg (yield: 98%; optical purity: 84.4% e.e.) of the title compound was obtained by the same manner as described in the Example 3.

Industrial Applicability

As described above, according to the present invention, it is provided the optically active pyrrolo[3,2-c]azepine derivatives having a hydroxyl group at the 8-position useful as cardiovascular drugs or raw materials as well as intermediates for synthesis of those drugs from their precursors, i.e., ketone compounds having carbonyl group at the 8-position, by the simple asymmetric reduction in high chemical and optical yields.

Therefore, the method for preparing the optically active pyrrolo[3,2-c]azepine derivatives of the present invention is quite useful as industrial applicable procedures.

What is claimed is:

1. A method for preparing the optically active pyrroloazepine compounds represented by formula (I):

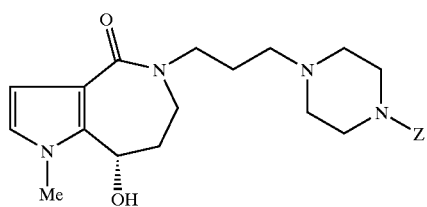

(I)

wherein Z represents an optionally substituted phenyl group, said method comprising;
asymmetrically reducing a ketone represented by formula (II):

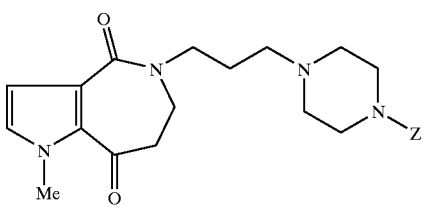

(II)

with a metal hydride and an alcohol in the presence of an optically active cobalt complex catalyst, and purifying the resulting compound.

2. A method for preparing the optically active pyrroloazepine compounds represented by formula (I):

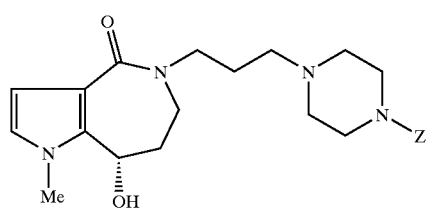

(I)

wherein Z represents an optionally substituted phenyl group, said method comprising;
asymmetrically reducing a ketone represented by formula (III):

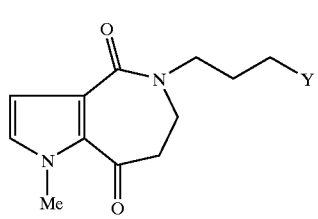

(III)

wherein Y represents a halogen atom, with a metal hydride and an alcohol in the presence of an optically active cobalt complex catalyst to obtain the optically active alcohol represented by formula (IV):

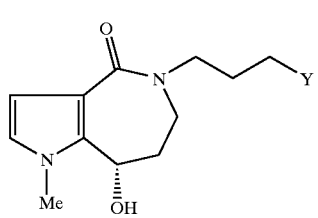

(IV)

reacting the resulting alcohol compound of the formula (IV) with the piperazine compound represented by formula (V) or a salt thereof:

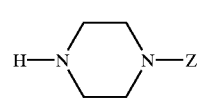

(V)

and purifying the resulting compound.

3. A method for preparing the optically active pyrroloazepine compounds represented by formula (IV):

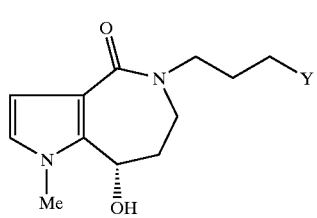

(IV)

wherein Y represents a halogen atom, said method comprising asymmetrically reducing the ketone compound represented by formula (III):

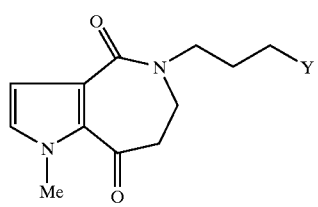

(III)

wherein Y represents a halogen atom, with a metal hydride and an alcohol in the presence of an optically active cobalt complex catalyst.

4. A method for preparing optically active pyrroloazepine compounds according to claim 1, wherein the optically active cobalt complex catalyst comprises a ligand which is an enantiomer of formula (VI):

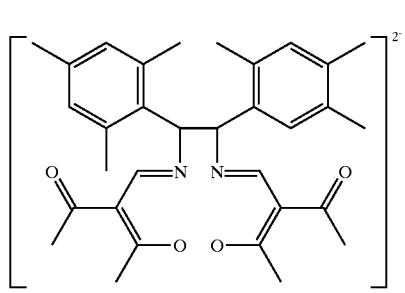

(VI)

wherein formula (VI) represents an optically active compound, in
which two mesityl groups are located trans to each other, in which said enantiomer is derived from the protonated levorotatory compound represented by formula (VII):

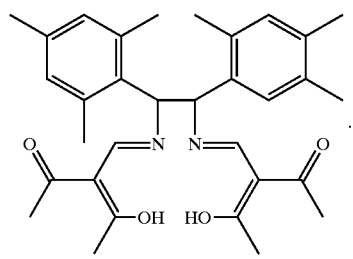

(VII)

5. A method for preparing optically active pyrroloazepine compounds according to claim 2, wherein the optically active cobalt complex catalyst comprises a ligand which is an enantiomer of formula (VI):

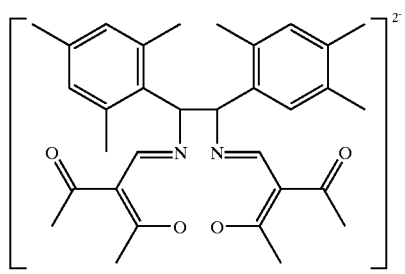

(VI)

wherein formula (VI) represents an optically active compound, in
which two mesityl groups are located trans to each other, in which said enantiomer is derived from the protonated levorotatory compound represented by formula (VII):

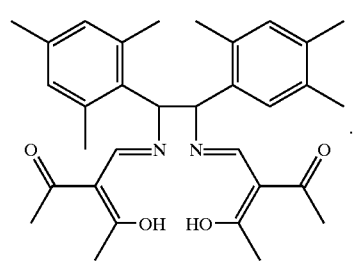

(VII)

6. A method for preparing optically active pyrroloazepine compounds according to claim 3, wherein the optically active cobalt complex comprises a ligand which is an enantiomer of formula (VI):

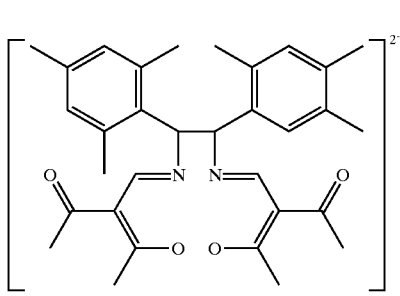

(VI)

wherein formula (VI) represents an optically active compound,
in which two mesityl groups are located trans to each other, in which said enantiomer is derived from the protonated levorotatory compound represented by formula (VII):

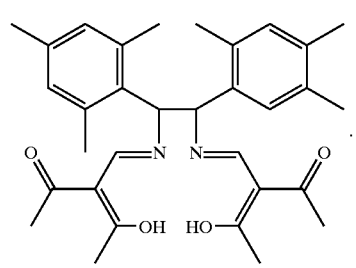

(VII)

7. A method for preparing optically active pyrroloazepine compounds according to claim 1, wherein cobalt of the optically active cobalt complex catalyst is divalent cobalt or trivalent cobalt.

8. A method for preparing optically active pyrroloazepine compounds according to claim 2, wherein cobalt of the optically active cobalt complex catalyst is divalent cobalt or trivalent cobalt.

9. A method for preparing optically active pyrroloazepine compounds according to claim 3, wherein cobalt of the optically active cobalt complex catalyst is divalent cobalt or trivalent cobalt.

10. A method for preparing optically active pyrroloazepine compounds according to claim 1, wherein the alcohol is tetrahydrofurfuryl alcohol.

11. A method for preparing optically active pyrroloazepine compounds according to claim 2, wherein the alcohol is tetrahydrofurfuryl alcohol.

12. A method for preparing optically active pyrroloazepine compounds according to claim 3, wherein the alcohol is tetrahydrofurfuryl alcohol.

13. A method for preparing optically active pyrroloazepine compounds according to claim 1, wherein the asymmetric reduction is conducted in a solvent containing tetrahydrofuran.

14. A method for preparing optically active pyrroloazepine compounds according to claim 2, wherein the asymmetric reduction is conducted in a solvent containing tetrahydrofuran.

15. A method for preparing optically active pyrroloazepine compounds according to claim 3, wherein the asymmetric reduction is conducted in a solvent containing tetrahydrofuran.

16. A method for preparing optically active pyrroloazepine compounds according to claim 4, wherein cobalt of the optically active cobalt complex catalyst is divalent cobalt or trivalent cobalt.

17. A method for preparing optically active pyrroloazepine compounds according to claim 5, wherein cobalt of the optically active cobalt complex catalyst is divalent cobalt or trivalent cobalt.

18. A method for preparing optically active pyrroloazepine compounds according to claim 6, wherein cobalt of the optically active cobalt complex catalyst is divalent cobalt or trivalent cobalt.

19. A method for preparing optically active pyrroloazepine compounds according to claim 4, wherein the alcohol is tetrahydrofurfuryl alcohol.

20. A method for preparing optically active pyrroloazepine compounds according to claim 5, wherein the alcohol is tetrahydrofurfuryl alcohol.

21. A method for preparing optically active pyrroloazepine compounds according to claim 6, wherein the alcohol is tetrahydrofurfuryl alcohol.

22. A method for preparing optically active pyrroloazepine compounds according to claim 7, wherein the alcohol is tetrahydrofurfuryl alcohol.

23. A method for preparing optically active pyrroloazepine compounds according to claim 8, wherein the alcohol is tetrahydrofurfuryl alcohol.

24. A method for preparing optically active pyrroloazepine compounds according to claim 9, wherein the alcohol is tetrahydrofurfuryl alcohol.

25. A method for preparing optically active pyrroloazepine compounds according to claim 16, wherein the alcohol is tetrahydrofurfuryl alcohol.

26. A method for preparing optically active pyrroloazepine compounds according to claim 17, wherein the alcohol is tetrahydrofurfuryl alcohol.

27. A method for preparing optically active pyrroloazepine compounds according to claim 18, wherein the alcohol is tetrahydrofurfuryl alcohol.

28. A method for preparing optically active pyrroloazepine compounds according to claim 4, wherein the asymmetric reduction is conducted in a solvent containing tetrahydrofuran.

29. A method for preparing optically active pyrroloazepine compounds according to claim 5, wherein the asymmetric reduction is conducted in a solvent containing tetrahydrofuran.

30. A method for preparing optically active pyrroloazepine compounds according to claim 6, wherein the asymmetric reduction is conducted in a solvent containing tetrahydrofuran.

31. A method for preparing optically active pyrroloazepine compounds according to claim 7, wherein the asymmetric reduction is conducted in a solvent containing tetrahydrofuran.

32. A method for preparing optically active pyrroloazepine compounds according to claim 8, wherein the asymmetric reduction is conducted in a solvent containing tetrahydrofuran.

33. A method for preparing optically active pyrroloazepine compounds according to claim 9, wherein the asymmetric reduction is conducted in a solvent containing tetrahydrofuran.

34. A method for preparing optically active pyrroloazepine compounds according to claim 16, wherein the asymmetric reduction is conducted in a solvent containing tetrahydrofuran.

35. A method for preparing optically active pyrroloazepine compounds according to claim 17, wherein the asymmetric reduction is conducted in a solvent containing tetrahydrofuran.

36. A method for preparing optically active pyrroloazepine compounds according to claim 18, wherein the asymmetric reduction is conducted in a solvent containing tetrahydrofuran.

37. A method for preparing optically active pyrroloazepine compounds according to claim 10, wherein the asymmetric reduction is conducted in a solvent containing tetrahydrofuran.

38. A method for preparing optically active pyrroloazepine compounds according to claim 11, wherein the asymmetric reduction is conducted in a solvent containing tetrahydrofuran.

39. A method for preparing optically active pyrroloazepine compounds according to claim 12, wherein the asymmetric reduction is conducted in a solvent containing tetrahydrofuran.

40. A method for preparing optically active pyrroloazepine compounds according to claim 19, wherein the asymmetric reduction is conducted in a solvent containing tetrahydrofuran.

41. A method for preparing optically active pyrroloazepine compounds according to claim 20, wherein the asymmetric reduction is conducted in a solvent containing tetrahydrofuran.

42. A method for preparing optically active pyrroloazepine compounds according to claim 21, wherein the asymmetric reduction is conducted in a solvent containing tetrahydrofuran.

43. A method for preparing optically active pyrroloazepine compounds according to claim 22, wherein the asymmetric reduction is conducted in a solvent containing tetrahydrofuran.

44. A method for preparing optically active pyrroloazepine compounds according to claim 23, wherein the asymmetric reduction is conducted in a solvent containing tetrahydrofuran.

45. A method for preparing optically active pyrroloazepine compounds according to claim 24, wherein the asymmetric reduction is conducted in a solvent containing tetrahydrofuran.

46. A method for preparing optically active pyrroloazepine compounds according to claim 25, wherein the asymmetric reduction is conducted in a solvent containing tetrahydrofuran.

47. A method for preparing optically active pyrroloazepine compounds according to claim 26, wherein the asymmetric reduction is conducted in a solvent containing tetrahydrofuran.

48. A method for preparing optically active pyrroloazepine compounds according to claim 27, wherein the asymmetric reduction is conducted in a solvent containing tetrahydrofuran.

* * * * *

UNITED STATES PATENT AND TRADEMARK OFFICE
CERTIFICATE OF CORRECTION

PATENT NO.   : 6,632,943 B2
DATED        : October 14, 2003
INVENTOR(S)  : Mizuno et al.

It is certified that error appears in the above-identified patent and that said Letters Patent is hereby corrected as shown below:

Column 4,
Lines 49-50, the formula should appear as follows:

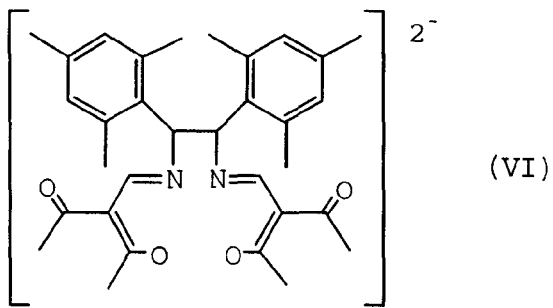

(VI)

Column 5,
Lines 2-11, the formula should appear as follows:

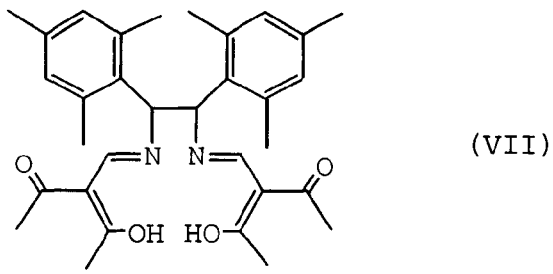

(VII)

Column 8,
Lines 34-45, the formula should appear as follows:

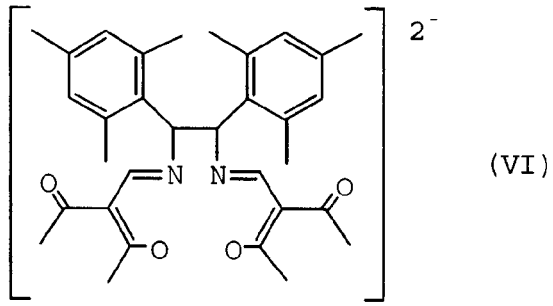

(VI)

UNITED STATES PATENT AND TRADEMARK OFFICE
CERTIFICATE OF CORRECTION

PATENT NO.   : 6,632,943 B2
DATED        : October 14, 2003
INVENTOR(S)  : Mizuno et al.

It is certified that error appears in the above-identified patent and that said Letters Patent is hereby corrected as shown below:

Column 8 (cont'd),
Lines 55-56, the formula should appear as follows:

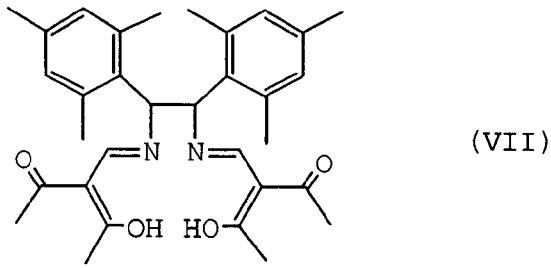

(VII)

Column 15,
Lines 18-29, the formula should appear as follows:

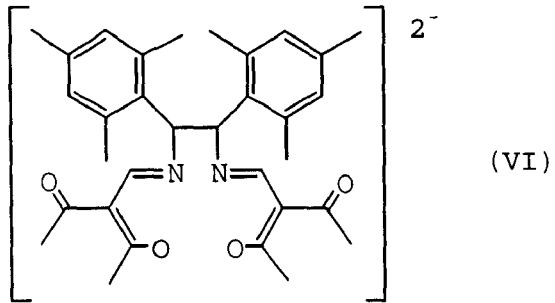

(VI)

Lines 36-47, the formula should appear as follows:

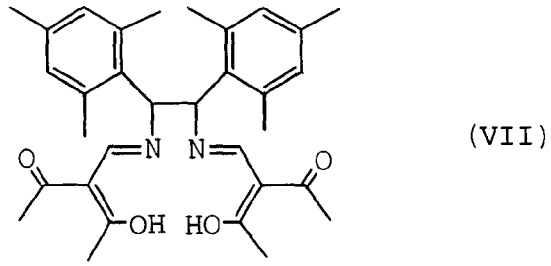

(VII)

UNITED STATES PATENT AND TRADEMARK OFFICE
CERTIFICATE OF CORRECTION

PATENT NO.     : 6,632,943 B2
DATED          : October 14, 2003
INVENTOR(S)    : Mizuno et al.

It is certified that error appears in the above-identified patent and that said Letters Patent is hereby corrected as shown below:

Column 15 (cont'd),
Lines 52-63, the formula should appear as follows:

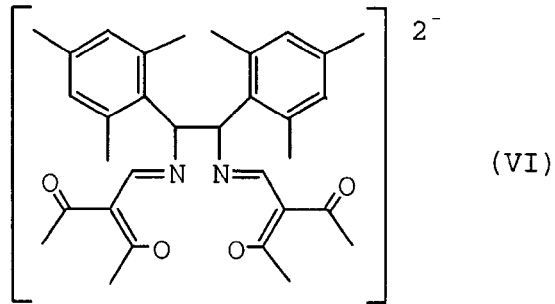

(VI)

Column 16,
Lines 4-13, the formula should appear as follows:

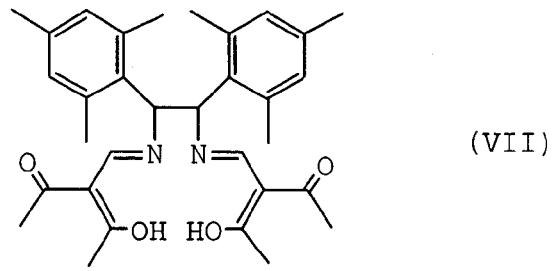

(VII)

UNITED STATES PATENT AND TRADEMARK OFFICE
CERTIFICATE OF CORRECTION

PATENT NO.   : 6,632,943 B2
DATED        : October 14, 2003
INVENTOR(S)  : Mizuno et al.

It is certified that error appears in the above-identified patent and that said Letters Patent is hereby corrected as shown below:

Column 16 (cont'd),
Lines 20-30, the formula should appear as follows:

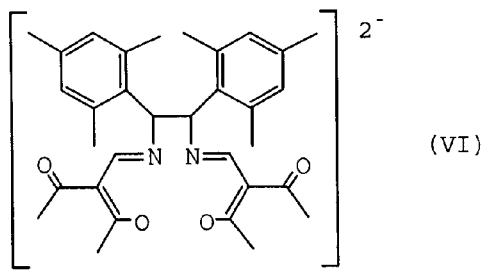

(VI)

Lines 37-48, the formula should appear as follows:

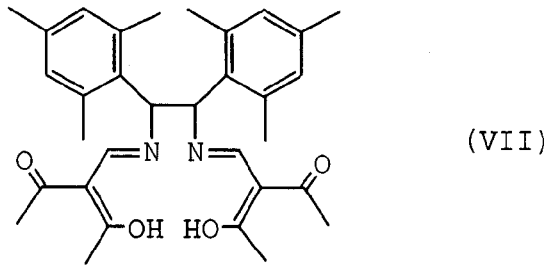

(VII)

Signed and Sealed this

Twenty-fourth Day of January, 2006

JON W. DUDAS
*Director of the United States Patent and Trademark Office*